United States Patent [19]

Altland et al.

[11] 4,093,462

[45] June 6, 1978

[54] 2,5-BIS(SECONDARY AMINO) OXA- AND THIADIAZOLE PHOTOGRAPHIC DEVELOPING AGENTS

[75] Inventors: Henry Wolf Altland; Stanley Wray Cowan, both of Rochester; Ismael Adolfo Olivares, Pittsford, all of N.Y.

[73] Assignee: Eastman Kodak Company, Rochester, N.Y.

[21] Appl. No.: 741,164

[22] Filed: Nov. 11, 1976

[51] Int. Cl.² ........................ G03C 5/30; C07D 277/38

[52] U.S. Cl. ................................ 96/66 HD; 96/29 R; 96/66 R; 96/76 R; 96/95; 260/306.8 D; 260/307 G

[58] Field of Search ................. 96/66 R, 29, 76 R, 95, 96/107, 66 HD; 260/306.8 D, 307 G

[56] References Cited

U.S. PATENT DOCUMENTS

| | | | |
|---|---|---|---|
| 2,915,395 | 12/1959 | Popeck et al. | 96/109 |
| 3,020,155 | 2/1962 | Yackel et al. | 96/29 R |
| 3,212,892 | 10/1965 | von König et al. | 96/66 R |
| 3,306,746 | 2/1967 | Schwarz | 96/66 R |
| 3,314,789 | 4/1967 | White et al. | 96/29 |

*Primary Examiner*—Mary F. Kelley
*Attorney, Agent, or Firm*—T. N. Dahl

[57] ABSTRACT

Oxa- and thiadiazole compounds substituted in the 2 and 5 positions with secondary amino groups are employed as photographic developing agents for exposed radiation-sensitive silver salts. The developing agents can be employed as components in developer compositions, as incorporated developing agents, and as developing agents in diffusion transfer processes.

23 Claims, No Drawings

2,5-BIS(SECONDARY AMINO) OXA- AND THIADIAZOLE PHOTOGRAPHIC DEVELOPING AGENTS

BACKGROUND OF THE INVENTION

1. Field of the Invention

This invention relates to photographic developing compositions, photographic developing processes, and photographic silver halide elements and emulsions with incorporated developing agents. In particular, the invention relates to certain oxa- and thiadiazole compounds as photographic silver halide developing agents.

2. Description of the Prior Art

Oxa- and thiadiazole compounds, including oxa- and thiadiazoles bearing appended amino or nitrogen-linked moieties, are well known for use in photographic processes. For example, in U.S. Pat. No. 3,306,746 (issued Feb. 28, 1967 to Moses A. Schwartz) sulfa substituted heterocyclic compounds, such as 2-methyl-5-sulfa-1,3,4-thiadiazole, are disclosed for use in developer compositions in conjunction with conventional developing agents. In U.S. Pat. No. 3,212,892 (issued Oct. 19, 1965 to Anita von König et al) a secondary amino mercapto thiadiazole is disclosed for use in preventing deposition of silver sludge on photographic elements as a consequence of developing with conventional developing agents. The thiadiazole disclosed, however, is said to have no influence on the photographic materials being processed in the disclosed developing solutions (see U.S. Pat. No. 3,212,892 supra at col. 1, lines 36–44). Mercapto thiadiazole compounds similar to those in U.S. Pat. No. 3,212,892, and mercapto oxadiazoles are the subject of British Patent 1,293,622 (published Oct. 18, 1972 and issued to Agfa-Gevaert Aktiengesellschaft) in which these compounds are said to stabilize silver images when employed in development baths in rapid photographic reproduction processes. Furthermore, a primary amino mercapto thiadiazole is disclosed in U.S. Pat. No. 3,020,155 (issued Feb. 6, 1962 to E. C. Yacket et al) for use in a diffusion transfer element to obtain black reproductions. The disclosed thiadiazole is said to be introducible into the diffusion transfer element by inclusion in a conventional developing solution.

The compounds discussed in the above patents, aside from being oxa- or thiadiazoles, bear only a single amino or nitrogen-linked moiety appended to the heterocyclic nucleus. In each instance, moreover, the disclosed compounds are employed only in conjunction with conventional developing agents. There is no suggestion in these patents that bis (secondary amino) thia- or oxadiazole compounds may be employed as photographic silver halide developing agents.

Further, in U.S. Pat. No. 2,915,395 (issued Dec. 1, 1959 to S. P. Popeck et al) 3,5-diureido-1,2,4-triazole and a water-soluble disulfonate thereof are disclosed as development accelerators for incorporation in a silver halide photographic emulsion in combination with a nitrobenzotriazole antifogging agent. This use of a dureido triazole, of course, does not suggest the use of bis(secondary amino) oxa- or thiadiazoles as photographic silver halide developing agents.

In the photographic field, there is continuing research underway to find new developing agents with broad utility. Not infrequently, compounds capable of reducing exposed silver salts are found, but for one reason or another their utility is severely limited. For example, the oxidized species of such compounds may be colored, causing undesirable "stain" in a photographic element processed with such compounds. Or, while desirably employed in a developer solution, a developing agent can be useless as an incorporated developing agent (i.e., one incorporated in a photographic emulsion) since it may be unstable in the emulsion. An incorporated developing agent may also cause spontaneous fogging of the silver salts, or may be lost by oxidation. Furthermore, even though compounds may exist which appear to avoid these problems, they may not have sufficient aqueous solubility or solubility in water-miscible solvents to enjoy commercial acceptance. Accordingly, developing agents having such universal applications are highly desirable.

SUMMARY OF THE INVENTION

In accordance with the invention, 2,5-bis(amino) diazole compounds of the formula

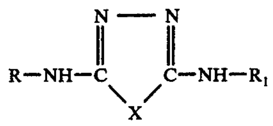

wherein R-NH— and —NH-$R_1$ are secondary amino groups, and X is sulfur or oxygen, are employed as photographic silver halide developing agents.

In one embodiment, a photographic silver halide developing composition comprising the above compound is provided. In another embodiment the described diazole is incorporated in a photographic silver halide emulsion. In a further embodiment it is incorporated in a silver halide emulsion layer or other layer of a photographic element. Development of elements incorporating the diazole defined herein can be activated either with alkaline solutions or with methylamine or ammonia vapors and the like. In yet another embodiment of the invention, a method of developing a photographic element having an exposed silver halide layer comprises developing the silver halide layer in the presence of a diazole silver halide developing agent described herein.

DESCRIPTION OF THE PREFERRED EMBODIMENTS

In accordance with the present invention, developing agents are provided which are bis(secondary amino-)oxa- or thiadiazoles. Compounds contemplated can be represented by the general structural formula:

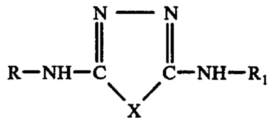

wherein R-NH— and —NH-$R_1$ are secondary amino moieties, and X is sulfur or oxygen. R-NH— and —NH-$R_1$ can each be the same secondary amino moiety or each can represent a different secondary amino moiety.

In accordance with the invention it has been discovered that the above-described diazoles possess the ability to reduce developable silver halide. It is believed, in this regard, that ionic silver in the presence of activator and the indicated developing agents is reduced to metallic silver according to the reaction:

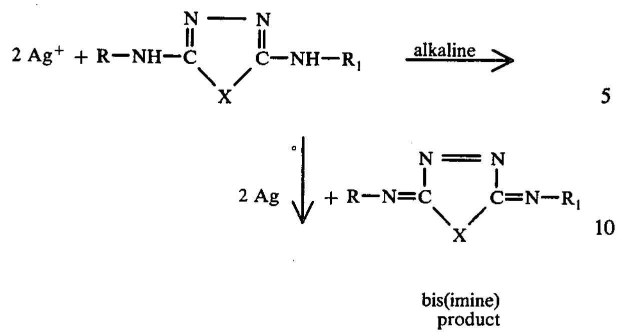

It is not intended, however, that applicants be bound by any theoretical explanation of the manner or mechanism whereby their invention functions.

Secondary amino groups, as included in the diazole developing agents of the invention, i.e, R-NH—, and $R_1$-NH—, can comprise a variety of aliphatic or aromatic moieties, and can be the same or different from each other. R and $R_1$ preferably ae electron-donating groups or groups which comprise electron-donating groups, as such groups are believed to facilitate the formation of the bis(imine) product of silver halide reduction above shown. Typical R and $R_1$ groups are alkyl groups containing 1-4 carbon atoms, such as methyl, ethyl, propyl and butyl, which alkyl can be either unsubstituted or substituted with alkoxy or alkylthio wherein the substituent alkyl contains 1 to 2 carbon atoms; aryl, preferably phenyl; alkoxy or alkylthio substituted aryl, wherein the alkyl group contains 1 to 2 carbon atoms; and alkenyl, preferably allyl.

Examples of typical 2,5-bisamino-1,3,4-oxa- or thiadiazole silver halide developing agents of this invention are listed in Table I.

TABLE I

| Compound | Name |
|---|---|
| 1. | 2,5-bis(methylamino)-1,3,4-thiadiazole |
| 2. | 2-methylamino-5-ethylamino-1,3,4-thiadiazole |
| 3. | 2,5-bis(ethylamino)-1,3,4-thiadiazole |
| 4. | 2,5-bis(n-butylamino)-1,3,4-thiadiazole |
| 5. | 2-allylamino-5-methylamino-1,3,4-thiadiazole |
| 6. | 2-(2-ethoxyethylamino)-5 methylamino-1,3,4-thiadiazole |
| 7. | 2,5-bis(phenylamino)-1,3,4-thiadiazole |
| 8. | 2,5-bis(2-methoxyethylamino)-1,3,4-thiadiazole |
| 9. | 2-(2-ethoxyethylamino)-5-(2-methoxyethylamino)-1,3,4-thiadiazole |
| 10. | 2,5-bis(2-ethoxyethylamino)-1,3,4-thiadiazole |
| 11. | 2-(2-methoxyethylamino)-5-phenylamino-1,3,4-thiadiazole |
| 12. | 2-(p-methoxyphenylamino)-5-(2-methoxyethylamino)-1,3,4-thiadiazole |
| 13. | 2-(3-methylthiopropylamino)-5-(2-methoxyethylamino)-1,3,4-thiadiazole |
| 14. | 2,5-bis(methylamino)-1,3,4-oxadiazole |
| 15. | 2,5-bis(ethylamino)-1,3,4-oxadiazole |

The preferred developing agents for use in accordance with the invention are compounds 1-3, 5, 6, 8-10, and 13-15 of Table I. It is also preferred that R and $R_1$ of the above formula be non-aromatic. The choice of particular compounds to provide optimum performance is, of course, dependent on the particular manner in which the compound is utilized. A given agent, for example, may be best suited for use as an incorporated agent whereas its use in a developer solution is less preferred (see Examples 12 and 32 below).

The described diazole silver halide developing agents are typically prepared by the acid-promoted cyclization of 2-thiobiureas or 2,5-dithiobiureas to the 2,5-bis(-secondary amino)-1,3,4-thiadiazoles, and of biureas to the 2,5-bis(secondary amino)-1,3,4-oxadiazoles. Agents employed in the cyclization include for example, acetic anhydride and phosphorus oxychloride. Exemplary preparation techniques are set forth in Example 49 of this application; in P. C. Guha, *Journal of the American Chemical Society,* 45, p. 1036 (1923); and in J. E. Oliver et al, *Journal of Medicinal Chemistry,* Vol. 15, No. 3, p. 315 (1972).

The developing agents of this invention can be suitably utilized in any of a variety of locations with respect to a photographic system. They can be employed in photographic processing solutions, for example, in an aqueous alkaline developer composition. They can be incorporated into a layer of a photographic element such as a silver halide emulsion layer, an overcoat layer or an interlayer. When employed as incorporated developing agents, the diazoles described herein, despite close association with photographic silver halide, do not spontaneously reduce the latter. When activated to reduce silver halide, such as by alkaline activation, moreover, the oxidized developing agents remain substantially colorless, thus avoiding undesirable stain.

The developing agents described herein can also be utilized in a developer composition intended for use in a diffusion transfer process or they can be utilized in one or more layers of a photographic element employed in a diffusion transfer process. Diffusion transfer processes and photographic elements in which the developing agents are useful are described, for example, in U.S. Pat. Nos. 2,352,014 of Rott issued June 20, 1944; 2,543,181 of Land issued Feb. 27, 1951; and 3,337,342 of Green issued Aug. 22, 1967. The developing agents of this invention can also be employed in so-called high-speed diffusion transfer processes as described, for example, in U.S. Pat. No. 3,326,683 of Land et al, issued June 20, 1967; or in other types of diffusion transfer processes such as those described in U.S. Pat. Nos. 2,857,274 of Land et al., issued Oct. 21, 1958; 3,020,155 of Yacket et al., issued Feb. 6, 1962; 2,584,030 of Land issued Jan. 29, 1952; and 2,923,623 of Land issued Feb. 2, 1960. These patents describe typical photographic products suitable for diffusion transfer systems employing (a) a photosensitive element which comprises a support having thereon at least one photosensitive silver salt emulsion layer (b) an image-receiving layer, and (c) a rupturable container containing an alkaline processing composition comprising a silver halide developing agent and, typically, a silver halide solvent.

Accordingly, one embodiment of the invention is a photographic silver halide developer composition (sometimes referred to as a processing composition) comprising a diazole silver halide developing agent as described herein. This is typically an aqueous alkaline solution.

Various development activators can be employed in the practice of the invention. These include any of those which provide the desired activation of the described developing agent. These include, for instance, alkaline development activators, such as inorganic alkalies including, for example, sodium hydroxide, potassium hydroxide, and lithium hydroxide; alkali metal carbonates such as sodium carbonate and potassium carbonate; alkali metal phosphates such as trisodium phosphate; and organic alkaline development activators such as quaternary ammonium bases and salts, amino alkanols and similar alkaline materials and/or alkali releasing materials. The described development activators can be applied to the described photographic element in any suitable manner including, for example, dipping, spraying and/or suitable surface application such as with rollers or with other mechanical means.

A range of concentrations of the described developing agent can be employed in a processing composition in the practice of the invention, depending on the desired image, the developing agent employed, processing conditions and the like. When employed in a processing composition, such as an aqueous solution, a concentration of about 0.1 mole to about 3.0 moles of developing agent per liter of processing composition is suitable. A concentration of about 0.5 to about 2.0 moles of developing agent per liter of processing composition is preferred.

The developing agents employed in the practice of the invention can be employed in combination with other silver halide developing agents. A developing agent described herein can be employed in such combination as auxiliary developing agent or as the main component of the developing combination. Suitable silver halide developing agents which can be employed in combination with the developing agents of this invention include, for example, polyhydroxybenzenes such as hydroquinone developing agents, e.g., hydroquinone; alkyl-substituted hydroquinones as exemplified by tertiary butylhydroquinone, methylhydroquinone and 2-5-dimethylhydroquinone catechols and pyrogallol; chloro-substituted hydroquinone such as chlorohydroquinone or dichlorohydroquinone; alkoxy-substituted hydroquinones such as methoxyhydroquinone or ethoxyhydroquinone; aminophenol developing agents, such as 2,4-diaminophenols and methylaminophenols; ascorbic acid developing acids such as ascorbic acid ketals, and ascorbic acid derivatives such as those described in U.S. Pat. No. 3,337,342 of Green issued Aug. 22, 1967; hydroxylamine developing agents such as N,N-di(2-ethoxyethyl)hydroxylamine; 3-pyrazolidone developing agents such as 1-phenyl-3-pyrazolidone and 4-methyl-4-hydroxymethyl-1-phenyl-3-pyrazolidone, including those described in British 930,572 published July 3, 1963; and acyl derivatives of para-aminophenol; such as described in British 1,045,303 published Oct. 12, 1966; hydroxytetronic acid and hydroxytetronimide developing agents; and cinnamic acid developing agents or lactone developing agent precursors described in Belgian Pat. 739,706; and the like.

The silver halide emulsions used with this invention can comprise silver chloride, silver bromide, silver bromoiodide, silver chlorobromiodide or mixtures thereof. The emulsions may be coarse or fine grain and can be prepared by any of the well-known procedures, e.g. single jet emulsions, double jet emulsions, such as Lippmann emulsions, ammoniacal emulsions, thiocyanate or thioether ripened emulsions such as those described in Nietz et al. U.S. Pat. No. 2,222,264 issued Nov. 4, 1940; Illingsworth U.S. Pat. No. 3,320,069 issued May 15, 1967; and McBride U.S. Pat. No. 3,271,157 issued Sept. 6, 1966. Surface image emulsions may be used or internal image emulsions such as those described in Davey et al U.S. Pat. No. 2,592,250 issued Apr. 8, 1952; Porter et al. U.S. Pat. No. 3,206,313 issued Sept. 14, 1965; Berriman U.S. Pat. No. 3,447,927 issued June 3, 1969. If desired, mixtures of surface and internal image emulsions may be used as described in Luckey et al U.S. Pat. No. 2,996,382 issued Apr. 15, 1961. Negative type emulsions may be used or direct positive emulsions such as those described in Leermakers U.S. Pat. No. 2,184,013 issued Dec. 19, 1930; Kendall et al. U.S. Pat. No. 2,541,472 issued Feb. 13, 1951; Berriman U.S. Pat. No. 3,367,778 issued Feb. 6, 1968; Schouwenaars British Pat. 723,019; Illingsworth et al. French Pat. 1,520,821; Ives U.S. Pat. No. 2,563,785 issued Aug. 7, 1951; Knott et al. U.S. Pat. No. 2,456,953 issued Dec. 21, 1968 and Land U.S. Pat. No. 2,861,885 issued Nov. 25, 1958. The emulsions may be regular grain emulsions such as the type described in Klein and Moisar, J. Phot. Sci., vol. 12, No. 5, Sept./Oct., 1965, pp. 242–251.

It is also advantageous in some cases to have an antifoggant present in the developer compositions of the invention. Suitable antifoggants include organic antifoggants, for example, benzotriazole, benzimidazole, 2-mercaptobenzimidazole and mercaptotetrazole antifoggants. The developer compositions of the invention can contain an inorganic antifoggant, such as potassium bromide, potassium iodide and/or sodium bromide. The photographic element processed can also contain an antifoggant although it has been demonstrated that elements incorporating the developing agents of this invention can be capable of good image discrimination without antifoggants. The concentration of antifoggant in either the photographic element processed or in the developer composition will vary depending upon the desired image characteristics, other components present, subsequent processing steps and the like. Usually less than about 2% by weight, e.g., 0.01% to about 2% by weight, antifoggant is suitable in the developer composition of the invention.

As previously noted, one embodiment of the invention is a photographic composition comprising a photographic silver halide and a bis(secondary amino) oxa- or thiadiazole silver halide developing agent, as described. This composition is typically a photographic silver halide emulsion.

A further embodiment is a photographic element comprising a support, photographic silver halide and bis(secondary amino) oxa- or thiadiazole silver halide developing agent, as described.

The concentration of developing agent in such compositions and elements can vary depending upon the desired image characteristics, particular developing agent employed, processing conditions and the like. A concentration of about 0.1 mole to about 4.0 moles of developing agent per mole of silver halide present is suitable.

A further embodiment of the invention is a photographic process comprising developing a latent image in an exposed photographic silver salt in the presence of a silver halide developing agent employing bis(secondary amino) oxa- or thiadiazole silver halide developing agent as described. Such development typically takes place in the presence of a suitable development activator, for example, an alkaline development activator.

Further information in regard to photographic systems in which the above described silver halide developing agents can be employed is found in Product Licensing Index, vol. 92, December, 1971, Publication 9232, pages 107–110, Paragraphs 1-XXV.

The following examples are included for a further understanding of the invention, in which reference will be made to the oxa- and thiadiazole silver halide developing agents listed in Table I.

EXAMPLES 1–15

A strip of fine grain silver bromoiodide positive film is sensitometrically exposed through a 0.15 density increment step wedge, that is a wedge commonly employed in the photographic art to provide a series of steps of increasing exposure. A tungsten light source (28 ergs/$cm^2$-sec) is employed. The resulting latent image is developed by immersing the photographic element in a silver halide developer having the following composition:

| | Mole |
|---|---|
| Developing agent | 0.02 |
| Sodium sulfite | 0.2 |
| Sodium hydroxide | 0.6 |
| Deaerated distilled water to 1.0 liter | |
| Mixed under a blanket of nitrogen | |
| 13.5 pH | |

Various developers are evaluated by employing individually developing agents from Table I. The activity of the developer is measured in terms of the time required to obtain a density of 2.0 on the fourth step of the strip of film. In some instances, a density of less than 2.0 is obtained in 16.0 minutes at which point development is stopped by removal of the film from the developer. Results are tabulated below.

TABLE II

| Example | Developing Agent | Time (min.) | Image Density |
|---|---|---|---|
| 1 | 1 | 2.6 | 2.00 |
| 2 | 2 | 1.4 | 2.00 |
| 3 | 3 | 3.1 | 2.00 |
| 4 | 4 | 16.0 | 0.70 |
| 5 | 5 | 1.0 | 2.00 |
| 6 | 6 | 1.3 | 2.00 |
| 7 | 7 | 16.0 | 0.02* |
| 8 | 8 | 1.7 | 2.00 |
| 9 | 9 | 1.8 | 2.00 |
| 10 | 10 | 2.0 | 2.00 |
| 11 | 11 | 16.0 | 1.03 |
| 12 | 12 | 16.0 | 0.94 |
| 13 | 13 | 1.5 | 2.00 |
| 14 | 14 | 4.9 | 2.00 |
| 15 | 15 | 6.7 | 2.00 |

*Low image density attributable to poor solubility of compound #7 in this particular developer solution.

Example 27 below, employing non-aqueous but water-miscible solvents, indicates compound 7 can be useful in developer solutions comprising appropriate co-solvents with water.

EXAMPLES 16–20

The relative staining propensity of representative compounds of the invention and of hydroquinone is examined.

Twenty mg. samples of selected developing agents from Table I and hydroquinone are placed in two sets of 10 ml. beakers. To one set is added 1 ml. each of a 4% sodium hydroxide solution; to the other set is added 1 ml. each of a solution comprising 4% sodium hydroxide and 6% sodium sulfite. Each solution is absorbed into a 1½ × 2 inch strip of chromatographic paper. The strips are placed in a museum jar over water for 24 hours at room temperature. The strips are dried and the densities read to neutral transmitted light on a densitometer. The density of an untreated paper base is subtracted to give net stain density. The results are summarized in Table III.

The low staining propensity of the developing agents of this invention is evident in the low density shown by this test.

TABLE III

| Example | Developing Agent | Net Stain Density | |
|---|---|---|---|
| | | No Sulfite | With Sulfite |
| 16 | 1 | 0.04 | 0.05 |
| 17 | 2 | 0.04 | 0.05 |
| 18 | 3 | 0.03 | 0.02 |
| 19 | 5 | 0.14 | 0.09 |
| 20 | Hydroquinone | 2.03 | 0.39 |

EXAMPLES 21–48

Aqueous mixtures each containing 0.00267 mole fine-grained silver chloride, 800 milligrams gelatin, 20 milligrams, nonylphenoxy polyglycidol surfactant, up to 2.0 milliliters N,N-dimethylformamide, and 0.008 mole each of a selected compound from Table I per 10.0 milliliters of total volume are coated and air-dried on subbed polyethylene-coated paper so that each square foot of coating contains approximately 40 milligrams silver. For comparison, a similar coating containing 0.008 mole hydroquinone as developing agent is also made. No spontaneous reduction of silver ions is noted with the coatings containing hydroquinone or the compounds of this invention.

A first strip cut from each of the coatings is exposed through a high-contrast test object and activated by immersing for five seconds in a solution containing 2.0 percent sodium hydroxide and 10.0 percent sodium sulfate. After activation, the strips are bathed in a hardening stop bath, washed and dried. The image and fog densities obtained are entered in Table IV.

TABLE IV

| Example | Compound No. | Image Density | Fog Density |
|---|---|---|---|
| 21 | 1 | 1.47 | 0.01 |
| 22 | 2 | 1.34 | 0.01 |
| 23 | 3 | 0.13 | 0.03 |
| 24 | 4 | 0.03 | 0.03 |
| 25 | 5 | 0.08 | 0.01 |
| 26 | 6 | 0.92 | 0.03 |
| 27 | 7 | 0.29 | 0.29 |
| 28 | 8 | 1.40 | 0.01 |
| 29 | 9 | 0.48 | 0.01 |
| 30 | 10 | 0.06 | 0.02 |
| 31 | 11 | 0.54 | 0.02 |
| 32 | 12 | 0.99 | 0.03 |
| 33 | 14 | 0.40 | 0.01 |
| 34 | Hydroquinone | 1.61 | 0.05 |

A second strip cut from each of the coatings is exposed through a high-contrast test object and activated by suspending over 40 percent aqueous methylamine in a closed container for one minute. The image and fog densities obtained are entered in Table V.

TABLE V

| Example | Compound No. | Image Density | Fog Density |
|---|---|---|---|
| 35 | 1 | 0.71 | 0.36 |
| 36 | 2 | 0.72 | 0.51 |
| 37 | 3 | 0.82 | 0.48 |
| 38 | 4 | 0.27 | 0.20 |
| 39 | 5 | 0.57 | 0.23 |
| 40 | 6 | 0.77 | 0.44 |
| 41 | 7 | 0.04 | 0.08 |
| 42 | 8 | 0.91 | 0.56 |
| 43 | 9 | 1.01 | 0.80 |
| 44 | 10 | 0.75 | 0.47 |
| 45 | 11 | 0.39 | 0.33 |
| 46 | 12 | 0.30 | 0.17 |
| 47 | 14 | 0.50 | 0.01 |
| 48 | Hydroquinone | 1.11 | 0.95 |

Results from Tables IV and V illustrate that silver halide developing agents of this invention are useful when incorporated in photographic silver halide emulsions and photographic elements comprising these emulsions. With some of these emulsions, it should be noted, one mode of activation is preferable to another. For example, emulsions incorporating compound 5 are preferably activated by methylamine vapors

EXAMPLE 49

This illustrates preparation of a representative developing agent of the invention (compound 5 of TABLE I).

A stirred suspension of allyl isothiocyanate (19.8 g, 0.2 mole) and of 4-methyl-3-thiosemicarbazide (21.0 g, 0.2 mole) in 150 ml denatured ethanol (5% methanol) was refluxed for one hour. The crystalline suspension was briefly chilled, and the 1-allyl-6-methyl-2,5-dithiobiurea was collected and vacuum dried. A stirred solution of this biurea (30.6 g, 0.15 mole) in phosphorous oxychloride (150 ml) was refluxed for 1½ hours. Unreacted phosphorus oxychloride was removed in vacuo, and the residue carefully partitioned between 1.2 M hydrochloric acid (150 ml) and chloroform (150 ml) while maintaining this mixture at 2° C with ice-bath cooling. The chloroform phase was extracted with another portion of 1.2 M hydrochloric acid (100 ml), and the combined acid layer was carefully made alkaline with conc. ammonium hydroxide. The resultant alkaline suspension was extracted with two portions of chloroform, and the combined chloroform extract was washed with a small portion of distilled water. After drying this chloroform extract over magnesium sulfate, the solvent was removed under reduced pressure to yield a colorless solid. Crystallization of the product from ethyl acetate gave 7.3 g (29 percent) of 2-allylamino-5-methylamino-1,3,4-thiadiazole (a colorless solid). Analysis confirmed the desired product.

The invention has been described in detail with particular reference to preferred embodiments thereof but it will be understood that variations and modifications can be effectd within the spirit and scope of the invention.

What is claimed is:

1. A photographic silver halide developer composition comprising a diazole silver halide developing agent of the formula:

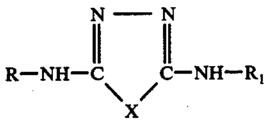

wherein each of R-NH— and —NH-$R_1$ is a secondary amino group, R and $R_1$ are independently selected from the group consisting of 1 to 4 carbon alkyl; 1 to 4 carbon alkyl substituted with alkoxy of 1 to 2 carbon atoms; 1 to 4 carbon alkyl substituted with alkylthio of 1 to 2 carbon atoms; aryl; aryl substituted with alkoxy of 1 to 2 carbon atoms; aryl substituted with alkylthio of 1 to 2 carbon atoms; and X is sulfur or oxygen.

2. The developer composition of claim 1 wherein X is sulfur, and each of R and $R_1$ is methyl; ethyl; propyl; methoxymethyl; methoxyethyl; methoxypropyl; ethoxymethyl; ethoxyethyl; ethoxypropyl; methylthiomethyl; methylthioethyl; methylthiopropyl; ethylthiomethyl; ethylthioethyl; ethylthiopropyl; or allyl.

3. The developer composition of claim 1 wherein said silver halide developing agent is 2,5-bis(methylamino)-1,3,4-thiadiazole;
2-methylamino-5-ethylamino-1,3,4-thiadiazole;
2,5-bis(ethylamino)-1,3,4-thiadiazole;
2-allylamino-5-methylamino-1,3,4-thiadiazole;
2-(2-ethoxyethylamino)-5-methylamino-1,3,4-thiadiazole;
2,5-bis(2-methoxyethylamino)-1,3,4-thiadiazole;
2-(2-ethoxyethylamino)-5-(2-methoxyethylamino)-1,3,4-thiadiazole;
2,5-bis(2-ethoxyethylamino)-1,3,4-thiadiazole;
2-(3-methylthiopropylamino)-5-(2-methoxyethylamino)-1,3,4-thiadiazole;
2,5-bis(methylamino)-1,3,4-oxadiazole; or
2,5-bis(ethylamino)-1,3,4-oxadiazole.

4. The developer composition of claim 1 wherein said silver halide developing agent is 2-(3-methylthiopropylamino)-5-(2-methoxyethylamino)-1,3,4-thiadiazole.

5. The developer composition of claim 1 further comprising an antifogging agent.

6. The developer composition of claim 2 further comprising a potassium bromide or benzotriazole antifogging agent.

7. The developer composition of claim 6 wherein said developing agent is 2-methylamino-5-ethylamino-1,3,4-thiadiazole; 2,5-bis(ethylamino)-1,3,4-thiadiazole; or 2,5-bis(2-ethoxyethylamino)-1,3,4-thiadiazole.

8. The developer composition of claim 1 wherein said composition is an aqueous solution comprising said developing agent and an alkaline development activator.

9. The developer composition of claim 8 wherein said solution has a pH of about 13.5.

10. A photographic element having incorporated therein a diazole silver halide developing agent of the formula:

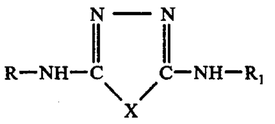

wherein each of R-NH— and —NH-$R_1$ is a secondary amino group, R and $R_1$ are independently selected from the group consisting of 1 to 4 carbon alkyl; 1 to 4 carbon alkyl substituted with alkoxy of 1 to 2 carbon atoms; 1 to 4 carbon alkyl substituted with alkylthio of 1 to 2 carbon atoms; aryl; aryl substituted with alkoxy of 1 to 2 carbon atoms; aryl substituted with alkylthio of 1 to 2 carbon atoms; and X is sulfur or oxygen.

11. The photographic element of claim 10 wherein X is sulfur and each of R and $R_1$ is methyl; ethyl; propyl; methoxymethyl; methoxyethyl; methoxypropyl; ethoxymethyl; ethoxyethyl; ethoxypropyl; methylthiomethyl; methylthioethyl; methylthiopropyl; ethylthiomethyl; ethylthioethyl; ethylthiopropyl; or allyl.

12. The photographic element of claim 10 wherein said silver halide developing agent is 2,5-bis(methylamino)-1,3,4-thiadiazole;
2-methylamino-5-ethylamino-1,3,4-thiadiazole;
2,5-bis(ethylamino)-1,3,4-thiadiazole;
2,5-bis(2-methoxyethylamino)-1,3,4-thiadiazole;
2-(2-ethoxyethylamino)-5-(2-methoxyethylamino)-1,3,4-thiadiazole;

2,5-bis(2-ethoxyethylamino)-1,3,4-thiadiazole;
2-(3-methylthiopropylamino)5-(2-methoxyethylamino)-1,3,4-thiadiazole;
2,5-bis(methylamino)-1,3,4-oxadiazole; or
2,5-bis(ethylamino)-1,3,4-oxadiazole.

13. The photographic element of claim 10 comprising a silver chloride emulsion layer incorporating a silver halide developing agent which is 2,5-bis-(methylamino)-1,3,4-thiadiazole; 2-methylamino-5-ethylamino-1,3,4,thiadiazole; 2-(2-ethoxyethylamino)-5-methylamino-1,3,4-thiadiazole; 2,5-bis(2-methoxyethylamino)-1,3,4-thiadiazole; 2-(2-ethoxyethylamino)-5-(2-methoxyethylamino)-1,3,4-thiadiazole; 2-(2-methoxyethylamino)-5-phenylamino-1,3,4-thiadiazole; 2-(p-methoxyphenylamino)-5-(2-methoxyethylamino)-1,3,4-thiadiazole; or 2,5-bis(methylamino)-1,3,4-oxadiazole.

14. The photographic element of claim 10 wherein said element is a diffusion transfer photosensitive element comprising a support having thereon at least one photosensitive silver salt emulsion layer, an image-receiving layer, and a rupturable container containing an alkaline processing composition comprising said diazole silver halide developing agent.

15. A photographic process comprising developing an imagewise exposed photographic silver halide layer in the presence of a silver halide developing agent of the formula:

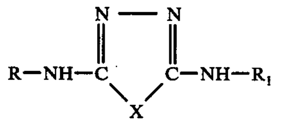

wherein each of R-NH— and —NH-$R_1$ is a secondary amino group, R and $R_1$ are independently selected from the group consisting of 1 to 4 carbon alkyl; 1 to 4 carbon alkyl substituted with alkoxy of 1 to 2 carbon atoms; 1 to 4 carbon alkyl substituted with alkylthio of 1 to 2 carbon atoms; aryl; aryl substituted with alkoxy of 1 to 2 carbon atoms; aryl substituted with alkylthio of 1 to 2 carbon atoms; and X is sulfur or oxygen.

16. A photographic process comprising developing an imagewise exposed photographic silver halide layer in the presence of a developer composition comprising a diazole silver halide developing agent of the formula:

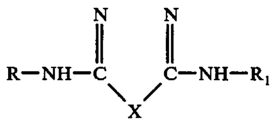

wherein each of R and $R_1$ is 1 to 4 carbon alkyl; alkoxy or alkylthio substituted 1 to 4 carbon alkyl wherein the substituent alkyl contains 1 to 2 carbon atoms; aryl; alkoxy or alkylthio substituted aryl wherein the substituent alkyl contains 1 to 2 carbon atoms; or alkenyl, and X is sulfur or oxygen.

17. The photographic process according to claim 16 wherein said silver halide developing agent is:

2,5-bis(methylamino)-1,3,4-thiadiazole;
2-methylamino-5-ethylamino-1,3,4-thiadiazole;
2,5-bis(ethylamino)-1,3,4-thiadiazole;
2-allylamino-5-methylamino-1,3,4-thiadiazole;
2-(2-ethoxyethylamino)-5-methylamino-1,3,4-thiadiazole;
2,5-bis(2-methoxyethylamino)-1,3,4-thiadiazole;
2-(2-ethoxyethylamino)-5-(2-methoxyethylamino)-1,3,4-thiadiazole;
2,5-bis(2-ethoxyethylamino)-1,3,4-thiadiazole;
2-(3-methylthiopropylamino)-5-(2-methoxyethylamino)-1,3,4-thiadiazole;
2,5-bis(methylamino)-1,3,4-oxadiazole; or
2,5-bis(ethylamino)-1,3,4-oxadiazole.

18. The photographic process according to claim 16 wherein said silver halide developing agent is 2-(3-methylthiopropylamino)-5-(2-methoxyethylamino)-1,3,4-thiadiazole.

19. The photographic process according to claim 17 wherein said silver halide layer is a silver bromoiodide layer.

20. A photographic process comprising developing an imagewise exposed photographic silver bromoiodide layer in the presence of a developer composition comprising (a) an alkaline development activator, (b) a silver bromoiodide developing agent which is 2-methylamino-5-ethylamino-1,3,4-thiadiazole; 2,5-bis(ethylamino)-1,3,4-thiadiazole or 2,5-bis(2-ethoxyethylamino)-1,2,4-thiadiazole; and (c) an antifogging agent which is potassium bromide or a benzotriazole.

21. A photographic process comprising developing an imagewise exposed photographic silver halide element in the presence of an alkaline development activator, said element having incorporated therein a diazole silver halide developing agent of the formula:

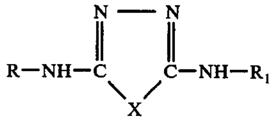

wherein each of R and $R_1$ is 1 to 4 carbon alkyl; alkoxy or alkylthio substituted 1 to 4 carbon alkyl wherein the substituent alkyl contains 1 to 2 carbon atoms; aryl; alkoxy or alkylthio substituted aryl wherein the substituent alkyl contains 1 to 2 carbon atoms; or alkenyl, and X is sulfur or oxygen, in the presence of an alkaline development activator.

22. The photographic process according to claim 21 wherein said silver halide developing agent is 2,5-bis(methylamino)-1,3,4-thiadiazole;
2-methylamino-5-ethylamino-1,3,4-thiadiazole;
2,5-bis(ethylamino)-1,3,4-thiadiazole;
2,5-bis(2-methoxyethylamino)-1,3,4-thiadiazole;
2-(2-ethoxyethylamino)-5-(2-methoxyethylamino)-1,3,4-thiadiazole;
2,5-bis(2-ethoxyethylamino)-1,3,4-thiadiazole;
2-(3-methylthiopropylamino)-5-(2-methoxyethylamino)-1,3,4-thiadiazole;
2,5-bis(methylamino)-1,3,4-oxadiazole; or
2,5-bis(ethylamino)-1,3,4-oxadiazole.

23. The photographic process according to claim 21 wherein said photographic element comprises a silver chloride emulsion layer and said silver halide developing agent is incorporated in said silver chloride layer and is 2,5-bis(methylamino)-1,3,4-thiadiazole; 2-methylamino-5-ethylamino-1,3,4-thiadiazole; 2-(2-ethoxyethylamino)-5-methylamino-1,3,4-thiadiazole; 2,5-bis(2-methoxyethylamino)-1,3,4-thiadiazole; 2-(2-ethoxyethylamino)-5-(2-methoxyethylamino)-1,3,4-thiadiazole; 2-(2-methoxyethylamino)-5-phenylamino-1,3,4-thiadiazole; 2-(p-methoxyphenylamino)-5-(2-methoxyethylamino)-1,3,4-thiadiazole; or 2,5-bis(methylamino)-1,3,4-oxadiazole.

* * * * *

UNITED STATES PATENT AND TRADEMARK OFFICE

CERTIFICATE OF CORRECTION

PATENT NO. : 4,093,462

DATED : June 6, 1978

INVENTOR(S) : H. W. Altland, S. W. Cowan, I. A. Olivares

It is certified that error appears in the above-identified patent and that said Letters Patent are hereby corrected as shown below:

Column 3, lines 6-10 (chemical products portion of indicated chemical reaction), change "2 Ag $\overset{O}{\downarrow}$" to --2 Ag $^{O}\downarrow$--;

line 22, "ae" should read --are--.

Column 4, line 38, change "Yacket" to --Yackel--.

Column 11, claim 16, the chemical formula for the diazole silver halide developing agent should read

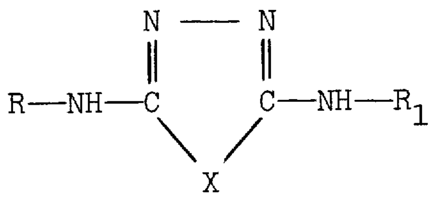

Signed and Sealed this

*Twenty-fourth* Day of *April 1979*

[SEAL]

*Attest:*

RUTH C. MASON
*Attesting Officer*

DONALD W. BANNER
*Commissioner of Patents and Trademarks*